(12) United States Patent
Mao et al.

(10) Patent No.: US 7,273,724 B1
(45) Date of Patent: Sep. 25, 2007

(54) POLYPEPTIDE-HUMAN ACTIN-BINDING PROTEIN 54 AND A POLYNUCLEOTIDE ENCODING THE SAME

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 856 days.

(21) Appl. No.: 10/130,742

(22) PCT Filed: Nov. 20, 2000

(86) PCT No.: PCT/CN00/00452

§ 371 (c)(1),
(2), (4) Date: May 23, 2002

(87) PCT Pub. No.: WO01/38382

PCT Pub. Date: May 31, 2001

(30) Foreign Application Priority Data

Nov. 23, 1999 (CN) .............. 99 1 24079

(51) Int. Cl.
- C12P 21/06 (2006.01)
- C12N 1/20 (2006.01)
- C12N 15/00 (2006.01)
- C07H 21/02 (2006.01)
- A61K 38/00 (2006.01)

(52) U.S. Cl. .............. 435/69.1; 536/23.1; 435/252.3; 435/320.1; 514/12

(58) Field of Classification Search ............... 530/350; 435/69.1, 252.3, 6, 320.1; 536/23.1; 514/12
See application file for complete search history.

(56) References Cited

FOREIGN PATENT DOCUMENTS

| EP | 905 239 | 3/1999 |
| JP | 9-191881 | 7/1997 |
| WO | 92/13000 | 8/1992 |
| WO | 99/23213 | 5/1999 |

OTHER PUBLICATIONS

Sasaki et al., J. Neurochem., 66(3), 980-988, 1996.*
International Search Report.

* cited by examiner

Primary Examiner—Maryam Monshipouri
(74) Attorney, Agent, or Firm—Crowell & Moring LLP

(57) ABSTRACT

The present invention discloses a novel polypeptide—human actin-binding protein 54 and a polynucleotide encoding the same, as well as a method of producing the polypeptide by DNA recombinant technology. The present invention also discloses methods of using the polypeptide in treatment of various diseases, such as malignant tumor, blood disease, HIV infection, immunological diseases and various inflammation. The present invention also discloses an antagonist against the polypeptide and the therapeutic use of the same. The present invention also discloses the use of such polynucleotide encoding human actin-binding protein 54.

11 Claims, 1 Drawing Sheet

```
Human actin-binding  1 MWTPRPALHVHVILYSPIHRCYARADPTMGRIWVDAAVPCLEECGFLLHFRDGCYHLETS    60
protein 54:            +WT   A+H    L S   RYA  P   I D+ P  +   L F++  Y L++
Retinall Fascin:    130 LWTVHLAIHPQAHLLSVSRRRYAHLCPQEDEIAADSNTPWGVDALVTLIFQNRQYCLKSC   189

Human actin-binding 61 THHFLSHVDRLFSQPSSQTAFHMQVRPGGLVALCDGEGGMLYPQGTHLLLGMGCNPMRG-  119
protein 54:            +L      RL  +P ++   + ++ + G L A  D +G  L P G     L  GN  G
Retinall Fascin:    190 DSRYLRSDGRLVWEPEARARYTLEFKAGKL-AFKDCDGHYLAPVGPAGTLRAGRNTRPGK  248

Human actin-binding 120 EEWFILQHCPTWVSLRSKTGRFISVIYDGEVRA-ASERLNRMSLFQFECDSESPTVQLRS  178
protein 54:            +E  F L+     V L +    R++SV      V A    E L+  + F   + D E+      S
Retinall Fascin:    249 DELFDLEESHPQVVLVAANHRYVSVRQGVNVSANQDEELDHET-FLMQIDQETKKCTFYS  307

Human actin-binding 179 ANGYYLSQRRHRAVMADGHPLESDTFFRMHWNCGRIILQSCRGRFLGIAPNSLLMANVIL  238
protein 54:            + G Y +    H  + A    +  +T F M W   R+ L++   GR++   + N  L A
Retinal Fascin:     308 STGGYWTLVTHGGIQATATQVSENTMFEMEWRGRRVALKASNGRYVCMKKNGQLAAISDF  367

Human actin-binding 239 PGPNEEFGILFANRSFLVLRGRYGYVGSSSGHDLIQCNQDQPDRIHLLPCRPGIYHFQAQ  298
protein 54:               G +EEF +    NR  LVLRG   G+V     G + +  N+   D  HL     G Y + +
Retinal Fascin:     368 VGEDEEFTLKLINRPILVLRGLDGFVCHRRGSNQLDTNRSVYDVFHL-SFSDGAYQIRGR  426

Human actin-binding 299 GGSFWSITSFGTFRPWGKFALNFCIELQGSNLLTVLAPNGFYMRADQSGTLLADSEGITR  358
protein 54:              GG  FW    S G+     G+ A +F  E +    L + A +G Y+R    SG  L   AD++
Retinal Fascin:     427 GGGFWHTGSHGSVCSDGERAEDFLFEFRERGRLAIRARSGKYLRGGASGLLRADADAPAG  486

Human actin-binding 359 ECIWEF 364
protein 54:               +WE+
Retinal Fascin:     487 VALWEY 492
```

```
Human actin-binding    1 MWTPRPALHVHVILYSPIHRCYARADPTMGRIWVDAAVPCLEECGFLLHFRDGCYHLETS   60
protein 54:              +WT   A+H    L S   R YA   P    I  D+  P   +   L  F++  Y L++
Retinall Fascin:       130 LWTVHLAIHPQAHLLSVSRRRYAHLCPQEDEIAADSNTPWGVDALVTLIFQNRQYCLKSC  189

Human actin-binding   61 THHFLSHVDRLFSQPSSQTAFHMQVRPGGLVALCDGEGGMLYPQGTHLLLGMGCNPMRG-  119
protein 54:              +L       RL +P  ++   +  ++  + G L A  D +G   L P G     L G N      G
Retinall Fascin:      190 DSRYLRSDGRLVWEPEARARYTLEFKAGKL-AFKDCDGHYLAPVGPAGTLRAGRNTRPGK  248

Human actin-binding  120 EEWFILQHCPTWVSLRSKTGRFISVIYDGEVRA-ASERLNRMSLFQFECDSESPTVQLRS  178
protein 54:              +E  F L+      V L +     R++SV      V A    E L+   +  F   + D E+         S
Retinall Fascin:      249 DELFDLEESHPQVVLVAANHRYVSVRQGVNVSANQDEELDHET-FLMQIDQETKKCTFYS  307

Human actin-binding  179 ANGYYLSQRRHRAVMADGHPLESDTFFRMHWNCGRIILQSCRGRFLGIAPNSLLMANVIL  238
protein 54:              + G Y +    H   + A      +  +T F M W     R+ L++  GR++   + N  L A
Retinal Fascin:       308 STGGYWTLVTHGGIQATATQVSENTMFEMEWRGRRVALKASNGRYVCMKKNGQLAAISDF  367

Human actin-binding  239 PGPNEEFGILFANRSFLVLRGRYGYVGSSSGHDLIQCNQDQPDRIHLLPCRPGIYHFQAQ  298
protein 54:                  G +EEF +      NR  LVLRG  G+V     G + +   N+       D  HL      G Y + +
Retinal Fascin:       368 VGEDEEFTLKLINRPILVLRGLDGFVCHRRGSNQLDTNRSVYDVFHL-SFSDGAYQIRGR  426

Human actin-binding  299 GGSFWSITSFGTFRPWGKFALNFCIELQGSNLLTVLAPNGFYMRADQSGTLLADSEGITR  358
protein 54:              GG  FW     S G+      G+  A +F   E +       L +  A  +G Y+R     SG  L    AD++
Retinal Fascin:       427 GGGFWHTGSHGSVCSDGERAEDFLFEFRERGRLAIRARSGKYLRGGASGLLRADADAPAG  486

Human actin-binding  359 ECIWEF  364
protein 54:                  +WE+
Retinal Fascin:       487 VALWEY  492
```

Fig. 1

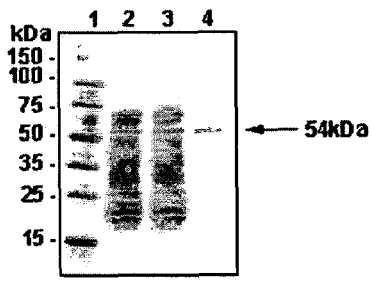

Fig. 2

POLYPEPTIDE-HUMAN ACTIN-BINDING PROTEIN 54 AND A POLYNUCLEOTIDE ENCODING THE SAME

CROSS-REFERENCE TO RELATED APPLICATIONS

This application is a 371(c) National Phase of International application Serial No. PCT/CN00/00452 filed Nov. 20, 2000, which claims priority to China patent application Serial No. 99124079.0 filed Nov. 23, 1999, the entire disclosures of which are hereby incorporated in their entireties.

FIELD OF INVENTION

The invention relates to the field of biotechnology. In particular, the invention relates to a novel polypeptide, human actin-binding protein 54, and a polynucleotide sequence encoding said polypeptide. The invention also relates to the method for the preparation and use of said polynucleotide and polypeptide.

TECHNICAL BACKGROUND

Fascins is a widely distributed protein family. It can concentrate F-actin filaments into bundles. (Edwards, R. A. et al., 1995 Cell Motil. Cytoskeleton 32, 1-9). The genes of fascins have been cloned from human, mice and *Xenopus*. (Duh, F. M. et al., 1994, DNA Cell Biol. 13:821-827; Edwards, R. A. et al., 1995, J. Biol. Chem. 270, 10764-10770; Holthuis, J. C. M. et al., 1994 Biochim. Biophys. Acta 1219: 184-188). As actin-binding protein, each fascin is expressed in many cellular structures such as micropodia and filopodia. The ubiquitous localization of fascins indicates their important function in morphogenesis of subcellular structures. In photoreceptor cells, actin is located in inner segment, synaptic terminal of the rod cells, the connecting cilium between inner segment and outer segment, the labial part of outer segment of rod cells, and the basal part of the rod outer segments. Actin plays an important role in these parts as to regulate morphogenesis of outer segment disk and in lower vertebrates shorten the photoreceptor to adjust to brightness (Williams, D. S. et al., 1988, J. Comp. Neurol. 272:161-176). As cell specific actin-binding proteins, fascins can help actin fulfill these functions.

There are three conservative domains in the fascin family of proteins. The largest one consist of twenty eight amino acid residues located in the N-terminal, and fifteen amino acid residues among these are almost completely conserved. The second one is the amino acid sequence ETFQLE in the middle of the full sequence. The third is the sequence GKYW near the C-terminal of the proteins.

Sequence analysis of a newly discovered protein reveals that it has all three conservative domains of the fascin family, with 92% of the conservative amino acids, and it is 95% homologous to human fascin. So the protein is a new member of fascin family. And because it is specifically expressed in photoreceptor cells, it was named retinal fascin (Yoshitsugu, S. et al., 1997 FEBS Lett. 414(2):381-6).

In addition to the three conservative domains, retinal fascin also has three highly conservative amino acid of fascin family—Gly 409, Ser 289 and Ser 39. Change of the first two amino acid will lead to functional loss of retinal fascin (Cant, K. et al., 1996, Genetics 143, 249-258). Ser39 is probably a phosphorylation site and phosphorylation of retinal fascin is very important for the organization of microfilaments and cell mobility (Yamakita, Y. et al., 1996, J. Biol. Chem. 271:12632-12638). The full length cDNA of retinal fascin is 1589 bp, including an open reading frame encoding a 492 aa. protein with an apparent molecular weight 55070 Da. There are neither N-terminal signal sequence nor transmembrane domain in retinal fascin.

Besides Ser39, retinal fascin also has phosphorylation sites for protein kinase A, protein kinase C and tyrosine kinase. These sites are: nine phosphorylation sites for protein kinase C—Thr20, Ser39, Ser147, Thr237, Ser272, The300, Thr375, Thr404, Thr465; and two phosphorylation sites for protein kinase A—Thr304, Ser399; two phosphorylation sites for Tyrosine kinase—Tyr193, Tyr228. These indicate that retinal fascin is regulated by phosphorylation.

The polypeptide of the present invention is 29% identical and 44% homogenous to retinal fascin at the protein level and has the three conservative domains of fascin family. So the polypeptide of the present is named "retinal fascin54" and is found to have similar biological functions with retinal fascin.

As discussed above, human actin-binding protein p54 plays an essential role in the regulation of important biological functions such as cell division and embryogenesis, and it's believed that many of proteins are involved in these regulations. So the determination of those related human actin-binding proteins, especially of their amino acid sequences is always desired in this filed. The isolation of this novel human actin-binding protein p54 builds the basis for research of the protein function under normal and clinical conditions, disease diagnosis and drug development. So the isolation of its cDNA is very important.

DISCLOSURE OF INVENTION

One objective of the invention is to provide an isolated novel polypeptide, i.e., a human actin-binding protein 54, and fragments, analogues and derivatives thereof.

Another objective of the invention is to provide a polynucleotide encoding said polypeptide.

Another objective of the invention is to provide a recombinant vector containing a polynucleotide encoding a human actin-binding protein 54.

Another objective of the invention is to provide a genetically engineered host cell containing a polynucleotide encoding a human actin-binding protein 54.

Another objective of the invention is to provide a method for producing a human actin-binding protein 54.

Another objective of the invention is to provide an antibody against a human actin-binding protein 54 of the invention.

Another objective of the invention is to provide mimetics, antagonists, agonists, and inhibitors for the polypeptide of the human actin-binding protein 54.

Another objective of the invention is to provide a method for the diagnosis and treatment of the diseases associated with an abnormality of human actin-binding protein 54.

The present invention relates to an isolated polypeptide, which is originated from human, and comprises a polypeptide having the amino acid sequence of SEQ ID NO: 2, or its conservative variants, or its active fragments, or its active derivatives and its analogues. Preferably, the polypeptide has the amino acid sequence of SEQ ID NO: 2.

The present invention also relates to an isolated polynucleotide, comprising a nucleotide sequence or its variant selected from the group consisting of (a) the polynucleotide encoding a polypeptide comprising the amino acid sequence of SEQ ID NO: 2; and (b) a polynucleotide complementary to the polynucleotide (a); (c) a polynucleotide that shares at least 70% homology to the polynucleotide (a) or (b). Preferably, said nucleotide sequence is selected from the group consisting of (a) the sequence of position 439-1533 in SEQ ID NO: 1; and (b) the sequence of position 1-1704 in SEQ ID NO: 1.

The invention also includes: a vector containing a polynucleotide of said invention, especially an expression vector; a host cell genetically engineered with the vector via transformation, transduction or transfection; a method for the production of said inventive polypeptide through the process of host cell cultivation and expression product harvest.

The invention also relates to an antibody which specifically binds to the inventive polypeptide.

The invention also relates to a method for selecting compounds which could simulate, activate, antagonize, or inhibit the activity of the inventive polypeptide and the compounds obtained by the method.

The invention also relates to a method for in vitro diagnosis method of the diseases or disease susceptibility related with the abnormal expression of the inventive polypeptide. The method involves the detection of mutation in the polypeptide or its encoding polynucleotide sequence, or the determination of its quantity and/or biological activity in biological samples.

The invention also relates to pharmaceutical compositions which comprises the inventive polypeptide, its analogues, mimetics, agonists, antagonists, inhibitors, and a pharmaceutically acceptable carrier.

The invention also relates to applications of the inventive polypeptide and/or its polynucleotide for drug development to treat cancers, developmental diseases, immune diseases, or other diseases caused by abnormal expression of the inventive polypeptide.

Other aspects of the invention are apparent to the skilled in the art in view of the disclosure set forth hereinbelow.

The terms used in this specification and claims have the following meanings, unless otherwise noted.

"Nucleotide sequence" refers to oligonucleotide, nucleotide, or polynucleotide and parts of polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in the invention is related to the sequence of a natural protein, the amino acid sequence of said "peptide" or "protein" will not be limited to be identical to the sequence of that natural protein.

"Variant" of a protein or polynucleotide refers to the amino acid sequence or nucleotide sequence, respectively with one or more amino acids or one or more nucleotides changed. Such changes include deletion, insertion, and/or substitution of amino acids in the amino acid sequence, or of nucleotides in the polynucleotide sequence. These changes could be conservative and the substituted amino acid has similar structural or chemical characteristics as the original one, such as the substitution of Ile with Leu. Changes also could be not conservative, such as the substitution of Ala with Trp.

"Deletion" refers to the deletion of one or several amino acids in the amino acid sequence, or of one or several nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing number of the residues.

"Biological activity" refers to structural, regulatory or biochemical characteristics of a natural molecule. Similarly, the term "immungenecity" refers to the ability of natural, recombinant, or synthetic proteins to inducing a specific immunological reaction, or of binding specific antibody in appropriate kind of animal or cell.

"Agonist" refers to molecules which regulate, but generally enhance the activity of the inventive polypeptide by binding and changing it. Agonists include proteins, nucleotides, carbohydrates or any other molecules which could bind the inventive polypeptide.

"Antagonist" or "inhibitor" refers to molecules which inhibit or down regulate the biological activity or immunogenicity the inventive polypeptide via binding to it. Antagonists or inhibitors include proteins, nucleotides, carbohydrates or any other molecules which bind to the inventive polypeptide.

"Regulation" refers to changes in function of the inventive polypeptide, including up-regulation or down-regulation of the protein activity, changes in binding specificity, changes of any other biological characteristics, functional or immune characteristics.

"Substantially pure" refers to the condition of substantially free of other naturally related proteins, lipids, saccharides, or other substances. One of ordinary skill in the art can purify the inventive polypeptide by standard protein purification techniques. Substantially pure polypeptide of the invention produces a single main band in a denaturing polyacrylamide gel. The purity of a polypeptide may also be analyzed by amino acid sequence analysis.

"Complementary" or "complementation" refers to the binding of polynucleotides by base pairing under the condition of approximate ion conditions and temperature. For instance, the sequence "C-T-G-A" could bind its complementary sequence "G-A-C-T." The complementation between two single strand molecules could be partial or complete. Homology or sequence similarity between two single strands obviously influences the efficiency and strength of the formed hybrid.

"Homology" refers to the complementary degree, which may be partially or completely homologous. "Partial homology" refers to a sequence being partially complementary to a target nucleotide. The sequence could at least partially inhibit the hybridization between a completely complementary sequence and the target nucleotide. Inhibition of hybridization could be assayed by hybridization (Southern blot or Northern blot) under less stringent conditions. Substantially complementary sequence or hybrid probe could compete with the completely complementary sequence and inhibit its hybridization with the target sequence under less stringent conditions. This doesn't mean that nonspecific binding is allowed under a less stringent condition, because specific or selective reaction is still required.

"Sequence Identity" refers to the percentage of sequence identity or similarity when two or several amino acid or nucleotide sequences are compared. Sequence identity may be determined by computer programs such as MEGALIGN (Lasergene Software Package, DNASTAR, Inc., Madison Wis.). MEGALIGN can compare two or several sequences using different methodologies such as the Cluster method (Higgins, D. G. and P. M. Sharp (1988) Gene 73:237-244). Cluster method examines the distance between all pairs and arrange the sequences into clusters. Then the clusters are partitioned by pair or group. The sequence identity between two amino acid sequences such as sequence A and B can be calculated by the following equation:

$$\frac{\text{Number of paired identical residues between sequences A and B}}{\text{Residue number of sequence A} - \text{number of gap residues in sequence A} - \text{number of gap residue in sequence B}} \times 100$$

Sequence identity between nucleotide sequences can also be determined by Cluster method or other well-known methods in the art such as the Jotun Hein method (Hein J., (1990) Methods in Enzymology 183:625-645)

"Similarity" refers to the degree of identity or conservative substitution degree of amino acid residues in corresponding sites of the amino acid sequences when compared to each other. Amino acids for conservative substitution are: negative charged amino acids including Asp and Glu; positive charged amino acids including Leu, Ile and Val; Gly and Ala; Asn and Gln; Ser and Thr; Phe and Tyr.

"Antisense" refers to the nucleotide sequences complementary to a specific DNA or RNA sequence. "Antisense strand" refers to the nucleotide strand complementary to the "sense strand."

"Derivative" refers to the inventive polypeptide or the chemically modified nucleotide encoding it. This kind of modified chemical can be derived from replacement of the hydrogen atom with Alkyl, Acyl, or Amino. The nucleotide derivative can encode peptide retaining the major biological characteristics of the natural molecule.

"Antibody" refers to the intact antibody or its fragments such as Fa, F(ab')2 and Fv, and it can specifically bind to antigenic epitopes of the inventive polypeptide.

"Humanized antibody" refers to an antibody which has its amino acid sequence in non-antigen binding region replaced to mimic human antibody and still retain the original binding activity.

The term "isolated" refers to the removal of a material out of its original environment (for instance, if it's naturally produced, original environment refers to its natural environment). For example, a naturally produced polynucleotide or a polypeptide in its original host organism means it has not been "isolated," while the separation of the polynucleotide or a polypeptide from its coexisting materials in natural system means it was "isolated." This polynucleotide may be a part of a vector, or a part of a compound. Since the vector or compound is not part of its natural environment, the polynucleotide or peptide is still "isolated."

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated human actin-binding protein 54," means that human actin-binding protein 54 does not essentially contain other proteins, lipids, carbohydrate or any other substances associated therewith in nature. The skilled in the art can purify human actin-binding protein 54, by standard protein purification techniques. The purified polypeptide forms a single main band on a non-reducing PAGE gel. The purity of human actin-binding protein 54 can also be analyzed by amino acid sequence analysis.

The invention provides a novel polypeptide—human actin-binding protein 54, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of human actin-binding protein 54. As used in the invention, the terms "fragment," "derivative" and "analogue" mean the polypeptide that essentially retains the same biological functions or activity of human actin-binding protein 54 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, including a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 1704 bp, whose ORF (439-1533) encodes 364 amino acids. Based on amino acid homology comparison, it is found that the encoded polypeptide is 32% homologous to hare R2D2 antigen. This novel human actin-binding protein 54 has similar structures and biological functions to those of the hare R2D2 antigen.

The polynucleotide according to the invention may be in the forms of DNA or RNA. The forms of DNA include cDNA, genomic DNA, and synthetic DNA, etc., in single stranded or double stranded form. DNA may be an encoding strand or a non-encoding strand. The coding sequence for mature polypeptide may be identical to the coding sequence shown in SEQ ID NO: 1, or is a degenerate sequence. As used herein, the term "degenerate sequence" means a sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/ 0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2

The invention also relates to nucleic acid fragments hybridized with the hereinabove sequence. As used in the present invention, the length of the "nucleic acid fragment" is at least more than 10 bp, preferably at least 20-30 bp, more preferably at least 50-60 bp, and most preferably at least 100 bp. The nucleic acid fragment can be used in amplification techniques of nucleic acid, such as PCR, so as to determine and/or isolate the polynucleotide encoding human actin-binding protein 54.

The polypeptide and polynucleotide of the invention are preferably in the isolated form, preferably purified to be homogenous.

According to the invention, the specific nucleic acid sequence encoding human actin-binding protein 54 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of human actin-binding protein 54 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleotides, preferably at least 30 nucleotides, more preferably at least 50 nucleotides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by human actin-binding protein 54 gene can be carried out by immunology methods, such as Western blotting, radioimmunoassay, and ELISA.

The method of amplification of DNA/RNA by PCR (Saiki, et al. Science 1985; 230:1350-1354) is preferably used to obtain the polynucleotide of the invention. Especially when it is difficult to obtain the full-length cDNA, the method of RACE (RACE-cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463-5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding human actin-binding protein 54, and a method for producing the polypeptide of the invention by recombinant techniques.

In the present invention, the polynucleotide sequences encoding human actin-binding protein 54 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of human actin-binding protein 54 and appropriate transcription/translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of *E. coli*; PL promoter of λ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for *E. coli*.

An ordinarily skilled in the art know clearly how to select appropriate vectors, transcriptional regulatory elements, e.g., promoters, enhancers, and selective marker genes.

According to the invention, polynucleotide encoding human actin-binding protein 54 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as *E. coli, Streptomyces, Salmonella typhimurium*; fungal cells, such as yeast; plant cells; insect cells such as *Drosophila* S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as *E. coli*, competent cells, which are capable of DNA uptake, can be prepared from cells harvested after exponential growth phase and subsequently treated by the $CaCl_2$ method using procedures well known in the art. Alternatively, MgCl2 can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant human actin-binding protein 54 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human actin-binding protein 54 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and a combination thereof.

BRIEF DESCRIPTION OF THE DRAWINGS

The following drawings are provided to illustrate the embodiment of the invention, not to limit the scope of invention defined by the claims.

FIG. 1 shows an alignment comparison of amino acid sequences of human actin-binding protein 54 of the invention and retinal fascin. The upper sequence is human actin-binding protein 54, and the lower sequence is Retinal fascin. The identical and similar amino acids are indicated by a one-letter code of amino acid and "+" respectively.

FIG. 2 shows the SDS-PAGE of the isolated human actin-binding protein 54, which has a molecular weight of 54 kDa. The isolated protein band is marked with an arrow.

BEST MODE FOR CARRYING OUT THE INVENTION

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Cloning of Human Actin-Binding Protein 54 Gene

Total RNA from a human embryonic brain was extracted by the one-step method with guanidinium isocyanate/phenol/chloroform. The poly(A) mRNA was isolated from the total RNA with Quik mRNA Isolation Kit (Qiegene). cDNA was prepared by reverse transcription with 2 μg poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 1030c03 was found to be a novel DNA sequence. The inserted cDNA sequence of clone 1030c03 was dual-directionally sequenced with a serial of synthesized primers. It was indicated that the full length cDNA contained in clone 1030c03 was 1704 bp (SEQ ID NO: 1) with a 1094 bp ORF located in positions 439-1533 which encoded a novel protein (SEQ ID NO: 2). This clone was named pBS-1030c03 and the encoded protein was named human actin-binding protein 54.

EXAMPLE 2

Homology Search of cDNA Clone

The homology research of the DNA sequence and its protein sequence of human actin-binding protein 54 of the invention were performed by Blast (Basic local Alignment search tool) (Altschul, SF et al. J. Mol. Biol. 1990; 215: 403-10) in databases such as Genbank, Swissport, etc. The most homologous gene to human actin-binding protein 54 of the invention is known Retinal Fascin. The Genbank accession number of its encoded protein is AB003485. The alignment result of the protein was shown in FIG. 1. Two proteins are highly homologous with an identity of 29% and a similarity of 44%.

EXAMPLE 3

Cloning Human Actin-Binding Protein 54 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:
Primer 1: 5'-GAGGGGATAGTGGGAAAGTGGAA-3' (SEQ ID NO: 3)
Primer 2: 5'-GGGTGGCCTGTTGTGATGTATTG-3' (SEQ ID NO: 4)
Primer 1 is the forward sequence started from position 1 of 5' end of SEQ ID NO: 1.
Primer 2 is the reverse sequence of the 3' end of SEQ ID NO: 1.
The amplification condition was a 50 ul reaction system containing 50 mmol/L KCl, 10 mmol/L Tris-Cl (pH 8.5), 1.5 mmol/L $MgCl_2$, 200 mmol/L dNTP, 10 pmol of each primer, 1U Taq DNA polymerase(Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1-1704 bp of SEQ ID NO: 1.

EXAMPLE 4

Northern Blotting of Expression of Human Actin-Binding Protein 54 Gene

Total RNA was extracted by one-step method (Anal. Biochem 1987, 162, 156-159) with guanidinium isocyanate-phenol-chloroform. That is, homogenate the organize using 4M guanidinium isocyanate-25 mM sodium citrate, 0.2 sodium acetate(pH 4.0), add 1 volume phenol and ⅕ volume chloroform-isoamyl alcohol(49:1), centrifuge after mixing. Take out the water phase, add 0.8 volume isopropyl alcohol, then centrifuge the mixture. Wash the RNA precipitation using 70% ethanol, then dry, then dissolve it in the water. 20 μg RNA was electrophoresed on the 1.2% agarose gel containing 20 mM 3-(N-morpholino) propane sulfonic acid (pH 7.0)-5 mM sodium acetate-imM EDTA-2.2M formaldehyde. Then transfer it to a nitrocellulose filter. Prepare the 32P-labelled DNA probe with $\alpha$-$^{32}$P dATP by random primer method. The used DNA probe is the coding sequence (439 bp-1533 bp) of human actin-binding protein 54 amplified by PCR indicated in FIG. 1. The nitrocellulose filter with the transferred RNA was hybridized with the $^{32}$P-labelled DNA probe ($2\times10^6$ cpm/ml) overnight in a buffer containing 50% formamide-25 mM $KH_2PO_4$(Ph7.4)-5× Denhardt's solution and 200 μg/ml salmine. Then wash the filter in the 1×SSC-0.1% SDS, at 55° C., for 30 min. Then analyze and quantitative determinate using Phosphor Imager.

EXAMPLE 5

In Vitro Expression, Isolation and Purification of Recombinant Human Actin-Binding Protein 54

A pair of primers for specific amplification was designed based on SEQ ID NO: 1 and the encoding region in FIG. 1, the sequences are as follows:
Primer 3:5'-CCCCATATGATGTGGACCCCCCGAC-CAGCCCTCC-3'(SEQ ID NO: 5)
Primer 4: 5'-CCCGAATTCCTAAAATTCCCAGATA-CACTCTCTG-3'(SEQ ID NO: 6)
These two primers contain a NdeI and EcoRI cleavage site on the 5' end respectively. Within the sites are the coding sequences of the 5' and 3' end of the desired gene. NdeI and EcoRI cleavage sites were corresponding to the selective cleavage sites on the expression vector pET-28b(+) (Novagen, Cat. No. 69865.3). PCR amplification was performed with the plasmid pBS-1030c03 containing the full-length target gene as a template. The PCR reaction was subject to a 50 μl system containing 10 pg pBS-1030c03 plasmid, 10 pmol of Primer-3 and 10 pmol of Primer-4, 1 μl of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NdeI and EcoRI, the large fragments were recovered and ligated with T4 ligase. The ligated product was transformed into *E. coli* DH5α with the calcium chloride method. After cultured overnight on a LB plate containing a final concentration of 30 µg/ml kanamycin, positive clones were selected out using colony PCR and then sequenced. The positive clone (pET-1030c03) with the correct sequence was selected out and the recombinant plasmid thereof was transformed into BL21(DE3)plySs (Novagen) using the calcium chloride method. In a LB liquid medium containing a final concentration of 30 µg/ml of kanamycin, the host bacteria BL21(pET-1030c03) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—human actin-binding protein 54 was obtained by a His.Bind Quick Cartridge (Novagen) affinity column with binding 6His-Tag. SDS-PAGE showed a single band at 54 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

EXAMPLE 6

Preparation of Antibody Against Human Actin-Binding Protein 54

The following specific human actin-binding protein 54 polypeptide was synthesized by a polypeptide synthesizer (PE-ABI): NH$_2$-Met-Trp-Thr-Pro-Arg-Pro-Ala-Leu-His-Val-His-Val-Ile-Leu-Tyr-COOH (SEQ ID NO:7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvant 15 days later. The titer of antibody in the rabbit sera was determined with a titration plate coated with 15 µg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to human actin-binding protein 54.

EXAMPLE 7

Application of the Polynucleotide Fragments of the Invention as Hybridization Probes Oligonucleotides probes selected from the polynucleotide of the invention have many applications. The probe could be used to determine the existence of polynucleotide of the invention or its homologous polynucleotide sequences by hybridization with genomic, or cDNA library of normal or clinical tissues from varied sources. The probes could be further used to determine whether polynucleotide of the invention or its homologous polynucleotide sequences are abnormally expressed in cells from normal or clinical tissues.

The purpose of the following example is to select suitable oligonucletide fragments from SEQ ID NO:1 as hybridization probes to apply in membrane hybridization to determine whether there is polynucleotide of the invention or its homologous polynucleotide sequences in sample tissues. Membrane hybridization methods include dot blot, Southern blot, Northern blot, and replica hybridization. All methods follow nearly the same steps after the polynucleotide samples are immobilized on membranes. These steps are: membranes with immobilized samples are prehybridized in hybridization buffer not containing probes to block nonspecific binding sites of the membranes. Then the prehybridization buffer is replaced by hybridization buffer containing labeled probes and incubation is carried out at the appropriate temperature so probes hybridize with the target nucleotides. Free probes are washed off by a series of washing steps after the hybridization step. A high-stringency washing condition (relatively low salt concentration and high temperature) is applied in the example to reduce background and retain highly specific signals. Two types of probes are selected for the example: the first type of probes are oligonucleotides identical or annealed to SEQ ID NO:1; the second type probes are oligonucleotides partially identical or partially annealed to SEQ ID NO:1. Dot blot method is applied in the example for immobilization of the samples on membrane. The strongest specific signal produced by hybridization between first type probes and samples is obtained after relatively strict membrane washing steps.

Selection of Probes

The principles below should be followed for the selection of oligonucleotide fragments from SEQ ID NO:1 as hybrid probes:

1. The optimal length of probes should be between eighteen and fifty nucleotides.

2. GC amount should be between 30% and 70%, since nonspecific hybridization increases when GC amount is more than 70%.

3. There should be no complementary regions within the probes themselves.

4. Probes meeting the requirements above could be initially selected for further computer-aided sequence analysis, which includes homology comparison between the initially selected probes and its source sequence region (SEQ ID NO: 1), other known genomic sequences and their complements. Generally, the initial selected probes should not be used when they share fifteen identical continuous base pairs, or 85% homology with non-target region.

5. Whether the initially selected probes should be chosen for final application depends upon further experimental confirmation.

The following two probes could be selected and synthesized after the analysis above:

Probe One belongs to the first type, which is completely identical or annealed to the gene fragments of SEQ ID NO: 1 (41 nucleotides).

Probe Two belongs to the second type which is a substituted or mutant sequence of a fragment of SEQ ID NO: 1 (41 nucleotides).

Any other frequently used reagents unlisted but involved in the following experimental steps and their preparation methods can be found, for example, in: DNA PROBES G. H. Keller; M. M. Manak; Stockton Press, 1989 (USA) or a more commonly used molecular cloning experimental handbook *Molecular Cloning* (J. Sambrook et al. Academic press, 1998, 2nd edition).

Sample Preparation:

1. DNA Extraction from Fresh or Frozen Tissues

Steps: 1) Place fresh or newly thawed tissue onto a dish on ice containing phosphate-buffered saline (PBS). Cut the tissue into small pieces with scissors or an operating knife. Tissues should be kept damp through the operation. 2) Mince the tissue by centrifugation at 2,000 g for 10 minutes. 3) Re-suspend the pellet (about 10 ml/g) with cold homogenating buffer (0.25 mol/l saccharose; 25 mmol/l Tris-HCl, pH7.5; 25 m mol/LnaCl; 25 mmol/L MgCl2) at 4° C., and homogenate tissue suspension at full speed with an electronic homogenizer until it's completely smashed. 5) Centrifuge at 1,000 g for 10 minutes. 6) Re-suspend the cell pellet (1-5 ml per 0.1 g initial tissue sample), and centrifuge at 1,000 g for 10 minutes. 7) Re-suspend the pellet with lysis buffer (1-5 ml per 0.1 g initial tissue sample), and continue on to the phenol extraction method.

2. Phenol Extraction of DNA

Steps: 1) Wash cells with 1-10 ml cold PBS buffer and centrifuge at 1000 g for 10 minutes. 2) Re-suspend the precipitated cells with at least 100 µl cold cell lysis buffer ($1\times10^8$ cells/ml). 3) Add SDS to a final concentration of 1%. Addition of SDS into the cell precipitation before cell re-suspension will cause the formation of large balls by cells which is difficult to be smashed and total production will be reduced. This is especially important when extracting more than $10^7$ cells. 5) Incubate at 50° C. for an hour or shake gently overnight at 37° C. 6) Add an equal volume of phenol: chloroform: isoamyl alcohol (25:24:1) to the DNA solution to be purified in a microcentrifuge tube, and centrifuge for 10 minutes. If the two phases are not clearly separated, the solution should be recentrifuged. 7) remove the water phase to a new tube. 8) add an equal volume of chloroform: isoamyl alcohol (24:1) and centrifuge for 10 minutes. 9) remove the water phase containing DNA to a new tube and then purify DNA by ethanol precipitation.

3. DNA Purification By Ethanol Precipitation

Steps: 1) Add 1/10 vol of 2 mol/L sodium acetate and 2 vol of cold 100% ethanol into the DNA solution, mix and place at −20° C. for an hour or overnight. 2) Centrifuge for 10 minutes. 3) Carefully remove the ethanol. 4) Add 500 µl of cold 70% ethanol to wash the pellet and centrifuge for 5 minutes. 6) Carefully remove the ethanol and invert the tube on absorbent paper to remove remnant ethanol. Air dry for 10-15 minutes to evaporate the ethanol on the pellet surface. Do not dry the pellet completely since completely dry pellet is difficult to be dissolved again. 7) Re-suspend the DNA pellet with a small volume of TE or water. Spin at low speed or blow with a pipette, and add TE gradually and mix until DNA is completely dissolved. About 1 µl of DNA solution is obtained per $1\sim5\times10^6$ cells.

The following steps 8-13 are applied only when contamination must be removed, otherwise go directly to step 14. 8) Add Rnase A into DNA solution to a final concentration of 100 µg/ml and incubate at 37° C. for 30 minutes. 9) Add SDS and protease K to the final concentration of 0.5% and 100 µg/ml individually, and incubate at 37° C. for 30 minutes. 10) Add an equal volume of phenol: chloroform: isoamyl alcohol (25:24:1), and centrifuge for 10 minutes. 11) Carefully remove the water phase and extract it with an equal volume of chloroform: isoamyl alcohol (24:1) and centrifuge for 10 minutes. 12) Carefully remove out the water phase, and add 1/10 vol of 2 mol/L sodium acetate and 2.5 vol of cold 100% ethanol, then mix and place at −20° C. for an hour. 13) Wash the pellet with 70% ethanol and 100% ethanol, air dry and re-suspend DNA as same as the steps 3-6. 14) Determine the purity and production of DNA by A260 and A280 assay. 15) Separate DNA sample into several portions and store at −20° C.

Preparation of Sample Membrane

1) Take 4×2 pieces of nitrocellulose membrane (NC membrane) of desired size, and lightly mark out the sample dot sites and sample number with a pencil. Every probe needs two pieces of NC membrane, so then membranes could be washed under high stringency condition and moderate stringency condition individually in the following experimental steps.

2) Pipette 15 µl of samples and control individually, dot them on the membrane, and dry at room temperature.

3) Place the membranes on filter paper soaked in 0.1 mol/LnaOH, 1.5 mol/L NaCl, leave for 5 minutes (twice), and allow to dry. Transfer the membranes on filter paper soaked in 0.5 mol/L Tris-HCl (pH7.0), 3 mol/L NaCl, leave for 5 minutes (twice), and allow to dry.

4) place the membranes between clean filter paper, packet with aluminum foil, and vacuum dry at 60-80° C. for 2 hours.

Labeling of Probes

1) Add 3 µl probe (0.1 OD/10 µl), 2 µl kinase buffer, 8-10 uCi γ-32P-dATP+2U Kinase, and add water to the final volume of 20 µl.

2) Incubate at 37° C. for 2 hours.

3) Add 1/5 vol bromophenol blue indicator (BPB).

4) Load that sample on Sephadex G-50 column.

5) Collect the first peak before the elution of 32P-Probe (monitor the eluting process by Monitor).

6) Five drops each tube and collect for 10-15 tubes.

7) Measure the isotope amount with liquid scintillator.

8) Merged collection of the first peak is the prepared 32P-Probe (the second peak is free γ-32P-dATP).

Prehybridization

Place the sample membranes in a plastic bag, add 3-10 mg prehybrid buffer (10× Denhardt, s; 6×SSC, 0.1 mg/ml CT DNA (calf thymus gland DNA)), seal the bag, and shake on a 68° C. water bath for two hours hybridization.

Cut off a corner of the plastic bag, add in prepared probes, seal the bag, and shake on a 42° C. water bath overnight.

Membrane Washing

Membrane washing applying a high-stringency condition:
1) Take out the hybridized sample membranes
2) Wash the membranes with 2×SSC, 0.1% SDS at 40° C. for 15 minutes (twice).
3) Wash the membranes with 0.1×SSC, 0.1% SDS at 40° C. for 15 minutes (twice).
4) Wash the membranes with 0.1×SSC, 0.1% SDS at 55° C. for 30 minutes (twice), and dry at room temperature.

Membrane washing applying a low-stringency condition:
1) Take out the hybridized sample membranes.
2) Wash the membranes with 2×SSC, 0.1% SDS at 37° C. for 15 minutes (twice).
3) Wash the membranes with 0.1×SSC, 0.1% SDS at 37° C. for 15 minutes (twice).
4) Wash the membranes with 0.1×SSC, 0.1% SDS at 40° C. for 15 minutes (twice), and dry at room temperature.

X Ray Autoradiography:

X ray autoradiograph at −70° C. (autoradiograph time varies according to radioactivity of the hybrid spots).

Experimental Results:

In hybridization experiments carried out under low-stringency membrane washing condition, the radioactivity of all the above four probes hybridization spots show no obvious difference; while in hybridization experiments carried out under high-stringency membrane washing condition, radioactivity of the hybridization spot by Probe One is obviously stronger than the other three. So Probe One could be applied in qualitative and quantitative analysis of the existence and differential expression of the polynucleotide of the invention in different tissues.

INDUSTRIAL APPLICABILITY

The polypeptide of the invention and antagonists, agonists and inhibitors thereof can be directly used for the treatment of diseases, e.g., various malignant tumors or cancers, dermatitis, inflammation, adrenoprival disease and HIV infection and immune system diseases.

Retinal fascin is mainly expressed in eyes and its abnormal expression will cause a series of eye diseases. Meanwhile, as retinal fascin also is expressed in organs such as brain, heart, bones, muscle, intestine, and lung, its abnormal expression will lead to lesion of these organs, even causing cancers. Retinal fascin is also involved in signal transduction and regulation of development. The abnormal expression of human actin-binding protein P54 of the invention is concerned, will cause diseases including the following: retinitis, retinal pigmentation, bifid spine, cranioschisis, anencephadly, encephalocele, schizencephalic porencephaly, Down syndrome, congenital hydrocephalus, Aqueduct deformity, achondroplastic dwarf, spine epiphysis dysplasia, pseudo achondroplasia, Langer-Giedion syndrome, funnel chest, gonadal dysgenesis, Congenital adrenal hyperplasia, epispadia; Anaspadias, deformation syndromes accompanied by Microsomia such as Conradi syndrome and Danbolt-Closs syndrome, congenital glaucoma or cataract, congenital crystalline lens position abnormality, Congenital small palpebral fissure, retina dysplasia, Congenital optic atrophy, Congenital sensory nerve hearing loss, acrorhagadia, teratosis, Willams syndrome, Alagille syndrome, Bechwith-Wiedemann syndrome, Transient ischemic attacks, cerebral infarction, cerebral hemorrhage, subarachnoid hemorrhage, gliocytoma, meningioma, fibroneuroma, pituitary adenoma, intercranium granuloma, reflux esophagitis, esophageal carcinoma, gastritis (acute gastritis, chronic gastritis, other unusual gastritis such as acute corrosive gastritis, acute phlegmonous gastritis, Gastritis hypertrophic gigantica), peptic ulcer, gastric carcinoma, intestinal tuberculosis, CROHN disease, ulcerative colon, large intestines cancer, gastrointestinal neurosis (globus hystericus, psyche emesis, aerophagia, anorexia nervosa, irritable bowel syndrome), acute diarrhea, chronic hepatitis (Chronic persistent hepatitis, chronic active hepatitis), cirrhosis of liver (primary biliary cirrhosis), primary liver carcinoma, hepatic coma, pancreatitis (Acute pancreatitis, chronic pancreatitis), pancreatic carcinoma, tuberculous peritonitis, Upper digestive tract Massive bleeding, salivary gland tumor, esophageal carcinoma, esophageal leiomyosarcoma, primary oesophagus oat-cell carcinoma, gastric carcinoma, gastric malignant lymphoma, gastric carcinoid, cancer of colon, Intestinal malignant lymphoma, primary liver carcinoma, liver blastoma, primary carcinoma of gallbladder, pancreatic carcinoma, acute cardiac insufficiency, Chronic heart failure, sinus tachycardia, sinus bradycardia, sinus arrest, sinoatrial block, SSS, atrial premature beats, atrial tachycardia, atrial flutter, auricular fibrillation, atrio-ventricular junctional premature beat, atrio-ventricular junctional escape beat and cardiac rhythm, noparoxysmal supraventricular tachycardia, paroxysmal supraventricular tachycardia, WPW syndrome, ventricular premature beat, ventricular tachycardia, ventricular flutter, ventricular fibrillation, Atrioventricular block, intraventricular block, isolated pulmonic stenosis, aortic stenosis, coarctation of aorta, idiopathic dilatation of the pulmonary artery, primary pulmonary hypertension, persistent left superior vena cava, dextrocardia, primary hypertension, secondary hypertension, atherosclerosis, CAD (angina pectoris, myocardial infarction, latent coronary heart disease, cardiac insufficiency, arrhythmia coronary heart disease, and coronary heart disease of sudden death form), mitral stenosis, mitral incompetence, aortic stenosis, aortic incompetence, tricuspid stenosis, tricuspid incompetence, valvular pulmonary stenosis, pulmonary insufficiency, multiple valve disease, self-valve endocarditis, prosthetic valve endocarditis and vein drug addict's endocarditis, dilated cardiomyopathy, hypertrophic cardiomyopathy, Restrictive cardiomyopathy, myocarditis, alcoholic heart disease, perinatal heart disease, drug-induced heart disease, Keshan disease, Acute pericarditis, constrictive pericarditis, syphilitis cardiovascular disease, Takayasu arteritis, emphraxis milieu atherosclerosis, RAYNAUD syndrome, thrombophlebitis.

The invention also provides methods for screening compounds so as to identify an agent which enhances human actin-binding protein 54 activity (agonists) or decrease human actin-binding protein 54 activity (antagonists). The agonists enhance the biological functions of human actin-binding protein 54 such as inactivation of cell proliferation, while the antagonists prevent and cure the disorders associated with the excess cell proliferation, such as various cancers. For example, in the presence of an agent, the mammal cells or the membrane preparation expressing human actin-binding protein 54 can be incubated with the labeled human actin-binding protein 54 to determine the ability of the agent to enhance or repress the interaction.

Antagonists of human actin-binding protein 54 include antibodies, compounds, receptor deletants and analogues. The antagonists of human actin-binding protein 54 can bind to human actin-binding protein 54 and eliminate or reduce its function, or inhibit the production of human actin-binding protein 54, or bind to the active site of said polypeptide so that the polypeptide can not function biologically.

When screening for compounds as an antagonist, human actin-binding protein 54 may be added into a biological assay. It can be determined whether the compound is an antagonist or not by determining its effect on the interaction between human actin-binding protein 54 and its receptor. Using the same method as that for screening compounds, receptor deletants and analogues acting as antagonists can be selected. Polypeptide molecules capable of binding to human actin-binding protein 54 can be obtained by screening a polypeptide library comprising various combinations of amino acids bound onto a solid matrix. Usually, human actin-binding protein 54 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of human actin-binding protein 54. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with human actin-binding protein 54. Various adjuvants, including but are not limited to Freund's adjuvant, can be used to enhance the immunization. The techniques for producing human actin-binding protein 54 monoclonal antibodies include, but are not limited to, the hybridoma technique (Kohler and Milstein. Nature, 1975, 256:495-497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81:6851). Furthermore, techniques for producing a single-chain antibody (U.S. Pat. No. 4,946,778) are also useful for preparing single-chain antibodies against human actin-binding protein 54.

The antibody against human actin-binding protein 54 can be used in immunohistochemical method to detect the presence of human actin-binding protein 54 in a biopsy specimen.

The monoclonal antibody specific to human actin-binding protein 54 can be labeled by radioactive isotopes, and injected into human body to trace the location and distribution of human actin-binding protein 54. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to human actin-binding protein 54 can be covalently bound to bacterial or plant toxins, such as diphtheria toxin, ricin, ormosine. One common method is to challenge the amino group on the antibody with sulfhydryl cross-linking agents, such as SPDP, and bind the toxin onto the antibody by interchanging the disulfide bonds. This hybrid antibody can be used to kill human actin-binding protein 54-positive cells.

The antibody of the invention is useful for the therapy or the prophylaxis of disorders related to the human actin-binding protein 54. The appropriate amount of antibody can be administrated to stimulate or block the production or activity of human actin-binding protein 54.

The invention further provides diagnostic assays for quantitative and in situ measurement of human actin-binding protein 54 level. These assays are well known in the art and include FISH assay and radioimmunoassay. The level of human actin-binding protein 54 detected in the assay can be used to illustrate the importance of human actin-binding protein 54 in diseases and to determine the diseases associated with human actin-binding protein 54.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New human actin-binding protein 54 polynucleotides also have many therapeutic applications. Gene therapy technology can be used in the therapy of abnormal cell proliferation, development or metabolism, which are caused by the loss of human actin-binding protein 54 expression or the abnormal or non-active expression of human actin-binding protein 54. Recombinant gene therapy vectors, such as virus vectors, can be designed to express mutated human actin-binding protein 54 so as to inhibit the activity of endogenous human actin-binding protein 54. For example, one form of mutated human actin-binding protein 54 is a truncated human actin-binding protein 54 whose signal transduction domain is deleted. Therefore, this mutated human actin-binding protein 54 can bind the downstream substrate without the activity of signal transduction. Thus, the recombinant gene therapy vectors can be used to cure diseases caused by abnormal expression or activity of human actin-binding protein 54. The expression vectors derived from a virus, such as retrovirus, adenovirus, adeno-associated virus, herpes simplex virus, parvovirus, and so on, can be used to introduce the human actin-binding protein 54 gene into the cells. The methods for constructing a recombinant virus vector harboring human actin-binding protein 54 gene are described in the literature (Sambrook, et al. supra). In addition, the recombinant human actin-binding protein 54 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of the human actin-binding protein 54 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding human actin-binding protein 54 can be used in the diagnosis of human actin-binding protein 54 related diseases. The polynucleotide encoding human actin-binding protein 54 can be used to detect whether human actin-binding protein 54 is expressed or not, and whether the expression of human actin-binding protein 54 is normal or abnormal in the case of diseases. For example, human actin-binding protein 54 DNA sequences can be used in the hybridization with biopsy samples to determine the expression of human actin-binding protein 54. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The human actin-binding protein 54 specific primers can be used in RNA-polymerase chain reaction and in vitro amplification to detect transcripts of human actin-binding protein 54.

Further, detection of mutations in human actin-binding protein 54 gene is useful for the diagnosis of human actin-binding protein 54-related diseases. Mutations of human actin-binding protein 54 include site mutation, translocation, deletion, rearrangement and any other mutations compared with the wild-type human actin-binding protein 54 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15-35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes, human actin-binding protein 54 is administered in an amount, which is effective for treating and/or prophylaxis of the specific indication. The amount of human actin-binding protein 54 administrated on patient will depend upon various factors, such as delivery methods, the subject health, the judgment of the skilled clinician.

We claim:

1. An isolated polypeptide having an actin-binding protein 54 activity and comprising an amino acid sequence that is at least 95% identical to SEQ ID NO: 2.

2. The polypeptide of claim 1 wherein said polypeptide comprises the amino acid sequence of SEQ ID NO: 2.

3. An isolated polynucleotide selected from the group consisting of:
   (a) a polynucleotide encoding a polypeptide that has an actin-binding protein 54 activity and is at least 95% identical to SEQ ID NO: 2; or
   (b) a polynucleotide complementary to polynucleotide (a).

4. A polynucleotide of claim 3 wherein the polynucleotide encodes an amino acid sequence of SEQ ID NO:2.

5. A polynucleotide of claim 3 wherein the sequence of said polynucleotide comprises position 439-1533 of SEQ ID NO:1.

6. A polynucleotide of claim 5 wherein the sequence of said polynucleotide comprises position 1-1704 of SEQ ID NO:1.

7. A recombinant vector comprising a polynucleotide of claim 3, and a suitable regulatory element.

8. A genetically engineered host cell comprising a polynucleotide of claim 3.

9. A method for producing a polypeptide having an activity of an actin-binding protein 54 which comprises the steps of:
   (a) culturing an engineered host cell of claim 8 under conditions suitable for the expression of an actin-binding protein 54; and
   (b) isolating a polypeptide having the activity of an actin-binding protein 54 from the culture.

10. A composition comprising a polypeptide according to claim 1, and a pharmaceutically acceptable carrier.

11. A composition comprising a polynucleotide according to claim 3, and a pharmaceutically acceptable carrier.

* * * * *

SEQUENCE LISTING

```
<160> NUMBER OF SEQ ID NOS: 7

<210> SEQ ID NO 1
<211> LENGTH: 1704
<212> TYPE: DNA
<213> ORGANISM: Homo sapiens
<220> FEATURE:
<221> NAME/KEY: CDS
<222> LOCATION: (439)..(1533)
<223> OTHER INFORMATION:

<400> SEQUENCE: 1
gaggggatag tgggaaagtg gaagagctga cagcaaggag ataccagggc tgatgtggaa      60
gaggaggtgg ctggtgctga tgaaggtgcc agggtgatac cagccatgac agttgcaggg     120
ctccttggtc tggtaacttc gtgatactga tttccctctt ctccctcctg atgcctccag     180
acctgggaga tcttggtgag caatgagcat gagacacagg ccgtggtgcg actaaagagc     240
gtgcagggcc tctacctgct gtgtgagtgt gatggcaccg tgtgttatgg ccgcccaagg     300
```

-continued

```
accagccacc atgggtgctt tctactgcgt ttccaccgga acagcaagtg gaccctccag    360
tgcctaatct ctggtcgtta tttggagtcc aatggcaagg acgtgttttg cacttcccac    420
gtcctctcag cttaccac atg tgg acc ccc cga cca gcc ctc cat gtc cac      471
                    Met Trp Thr Pro Arg Pro Ala Leu His Val His
                     1               5                  10 gtg atc ctc tac agc ccc atc cac cgc tgc tat gcc cgg gct gac ccc      519
Val Ile Leu Tyr Ser Pro Ile His Arg Cys Tyr Ala Arg Ala Asp Pro
             15                  20                  25 act atg ggc cgc atc tgg gtg gac gca gca gtt ccc tgc ctg gag gag      567
Thr Met Gly Arg Ile Trp Val Asp Ala Ala Val Pro Cys Leu Glu Glu
         30                  35                  40 tgt ggc ttc ctg ttg cat ttc cga gat gga tgc tac cac ctg gag acc      615
Cys Gly Phe Leu Leu His Phe Arg Asp Gly Cys Tyr His Leu Glu Thr
     45                  50                  55 tct aca cac cac ttc ttg tcc cat gta gac cgg ctg ttc tcc caa ccc      663
Ser Thr His His Phe Leu Ser His Val Asp Arg Leu Phe Ser Gln Pro
 60                  65                  70                  75 tca tca cag aca gct ttt cac atg caa gtg cgg cct gga ggg ctt gtg      711
Ser Ser Gln Thr Ala Phe His Met Gln Val Arg Pro Gly Gly Leu Val
                 80                  85                  90 gca ctg tgt gat gga gaa gga ggc atg tta tat cca cag ggc acg cat      759
Ala Leu Cys Asp Gly Glu Gly Gly Met Leu Tyr Pro Gln Gly Thr His
             95                 100                 105 ctg ctc ttg ggc atg ggc tgc aac ccc atg agg ggt gag gag tgg ttc      807
Leu Leu Leu Gly Met Gly Cys Asn Pro Met Arg Gly Glu Glu Trp Phe
         110                 115                 120 atc cta cag cac tgc cca acc tgg gtc agc ctc agg tca aag act ggg      855
Ile Leu Gln His Cys Pro Thr Trp Val Ser Leu Arg Ser Lys Thr Gly
     125                 130                 135 cgg ttc atc tca gtc atc tac gat ggt gag gtg cgt gct gct tct gag      903
Arg Phe Ile Ser Val Ile Tyr Asp Gly Glu Val Arg Ala Ala Ser Glu
140                 145                 150                 155 cgc tta aac cga atg tcc ttg ttc cag ttt gaa tgt gac agt gag agc      951
Arg Leu Asn Arg Met Ser Leu Phe Gln Phe Glu Cys Asp Ser Glu Ser
                 160                 165                 170 ccc act gtg cag ctt cgt tca gcc aat ggc tac tac cta tcc cag agg      999
Pro Thr Val Gln Leu Arg Ser Ala Asn Gly Tyr Tyr Leu Ser Gln Arg
             175                 180                 185 cgc cac agg gca gta atg gct gat ggg cac ccc ctg gag tct gac acg     1047
Arg His Arg Ala Val Met Ala Asp Gly His Pro Leu Glu Ser Asp Thr
         190                 195                 200 ttc ttc cga atg cac tgg aac tgt ggc agg atc atc ctg cag tcc tgc     1095
Phe Phe Arg Met His Trp Asn Cys Gly Arg Ile Ile Leu Gln Ser Cys
     205                 210                 215 agg ggg cgc ttc ctg ggc att gca ccc aac agt ctg ctg atg gcc aat     1143
Arg Gly Arg Phe Leu Gly Ile Ala Pro Asn Ser Leu Leu Met Ala Asn
220                 225                 230                 235 gtc atc ctt cca ggc cca aat gag gaa ttt ggg att tta ttt gcc aat     1191
Val Ile Leu Pro Gly Pro Asn Glu Glu Phe Gly Ile Leu Phe Ala Asn
                 240                 245                 250 cgc tcc ttc ctt gta ttg cga ggt cgt tat ggc tat gtg ggc tcc tca     1239
Arg Ser Phe Leu Val Leu Arg Gly Arg Tyr Gly Tyr Val Gly Ser Ser
             255                 260                 265 tcg ggc cat gac ctc ata cag tgc aac cag gat cag ccc gac cgc att     1287
Ser Gly His Asp Leu Ile Gln Cys Asn Gln Asp Gln Pro Asp Arg Ile
         270                 275                 280 cat cta cta ccc tgc cga ccg ggt atc tac cac ttc cag gca cag ggg     1335
His Leu Leu Pro Cys Arg Pro Gly Ile Tyr His Phe Gln Ala Gln Gly
```

```
                    285                 290                 295
gga tcc ttc tgg tca ata aca tcc ttt ggc acc ttt cgc cct tgg ggc    1383
Gly Ser Phe Trp Ser Ile Thr Ser Phe Gly Thr Phe Arg Pro Trp Gly
300                 305                 310                 315 aag ttt gcc ctc aac ttc tgt atc gag ctt cag ggg agc aac tta ctc    1431
Lys Phe Ala Leu Asn Phe Cys Ile Glu Leu Gln Gly Ser Asn Leu Leu
            320                 325                 330 act gta ctg gcc ccc aat ggc ttc tac atg cga gcc gac caa agt ggc    1479
Thr Val Leu Ala Pro Asn Gly Phe Tyr Met Arg Ala Asp Gln Ser Gly
                335                 340                 345 acc ctg ttg gca gac agt gaa ggc att acc aga gag tgt atc tgg gaa    1527
Thr Leu Leu Ala Asp Ser Glu Gly Ile Thr Arg Glu Cys Ile Trp Glu
            350                 355                 360 ttt tag gtcaatggga tgtcacctac caaaatccaa atcctccagg aaaaactact     1583
Phe acactaaatg gaccaggaac ctcagagtca agatccaaga gaagaacatc tgttacaact  1643
tttcctaccc agtttagcaa aacacctgtt ttatgcaaca atacatcaca acaggccacc  1703
c                                                                  1704
```

<210> SEQ ID NO 2
<211> LENGTH: 364
<212> TYPE: PRT
<213> ORGANISM: Homo sapiens

<400> SEQUENCE: 2

```
Met Trp Thr Pro Arg Pro Ala Leu His Val His Val Ile Leu Tyr Ser
1               5                   10                  15

Pro Ile His Arg Cys Tyr Ala Arg Ala Asp Pro Thr Met Gly Arg Ile
            20                  25                  30

Trp Val Asp Ala Ala Val Pro Cys Leu Glu Glu Cys Gly Phe Leu Leu
        35                  40                  45

His Phe Arg Asp Gly Cys Tyr His Leu Glu Thr Ser Thr His His Phe
    50                  55                  60

Leu Ser His Val Asp Arg Leu Phe Ser Gln Pro Ser Ser Gln Thr Ala
65                  70                  75                  80

Phe His Met Gln Val Arg Pro Gly Gly Leu Val Ala Leu Cys Asp Gly
                85                  90                  95

Glu Gly Gly Met Leu Tyr Pro Gln Gly Thr His Leu Leu Gly Met
            100                 105                 110

Gly Cys Asn Pro Met Arg Gly Glu Glu Trp Phe Ile Leu Gln His Cys
        115                 120                 125

Pro Thr Trp Val Ser Leu Arg Ser Lys Thr Gly Arg Phe Ile Ser Val
    130                 135                 140

Ile Tyr Asp Gly Glu Val Arg Ala Ala Ser Glu Arg Leu Asn Arg Met
145                 150                 155                 160

Ser Leu Phe Gln Phe Glu Cys Asp Ser Glu Ser Pro Thr Val Gln Leu
                165                 170                 175

Arg Ser Ala Asn Gly Tyr Tyr Leu Ser Gln Arg Arg His Arg Ala Val
            180                 185                 190

Met Ala Asp Gly His Pro Leu Glu Ser Asp Thr Phe Phe Arg Met His
        195                 200                 205

Trp Asn Cys Gly Arg Ile Ile Leu Gln Ser Cys Arg Gly Arg Phe Leu
    210                 215                 220

Gly Ile Ala Pro Asn Ser Leu Leu Met Ala Asn Val Ile Leu Pro Gly
225                 230                 235                 240
```

-continued

```
Pro Asn Glu Glu Phe Gly Ile Leu Phe Ala Asn Arg Ser Phe Leu Val
                245                 250                 255

Leu Arg Gly Arg Tyr Gly Tyr Val Gly Ser Ser Ser Gly His Asp Leu
            260                 265                 270

Ile Gln Cys Asn Gln Asp Gln Pro Asp Arg Ile His Leu Leu Pro Cys
        275                 280                 285

Arg Pro Gly Ile Tyr His Phe Gln Ala Gln Gly Ser Phe Trp Ser
    290                 295                 300

Ile Thr Ser Phe Gly Thr Phe Arg Pro Trp Gly Lys Phe Ala Leu Asn
305                 310                 315                 320

Phe Cys Ile Glu Leu Gln Gly Ser Asn Leu Leu Thr Val Leu Ala Pro
                325                 330                 335

Asn Gly Phe Tyr Met Arg Ala Asp Gln Ser Gly Thr Leu Leu Ala Asp
            340                 345                 350

Ser Glu Gly Ile Thr Arg Glu Cys Ile Trp Glu Phe
        355                 360

<210> SEQ ID NO 3
<211> LENGTH: 23
<212> TYPE: DNA
<213> ORGANISM: Artificial
<220> FEATURE:
<223> OTHER INFORMATION: (oligonucleotide primer)

<400> SEQUENCE: 3
gaggggatag tgggaaagtg gaa                                            23

<210> SEQ ID NO 4
<211> LENGTH: 23
<212> TYPE: DNA
<213> ORGANISM: Artificial
<220> FEATURE:
<223> OTHER INFORMATION: (oligonucleotide primer)

<400> SEQUENCE: 4
gggtggcctg ttgtgatgta ttg                                            23

<210> SEQ ID NO 5
<211> LENGTH: 32
<212> TYPE: DNA
<213> ORGANISM: Artificial
<220> FEATURE:
<223> OTHER INFORMATION: (oligonucleotide primer)

<400> SEQUENCE: 5
cagccatggc ggggaagaag aatgttctgt cg                                  32

<210> SEQ ID NO 6
<211> LENGTH: 29
<212> TYPE: DNA
<213> ORGANISM: Artificial
<220> FEATURE:
<223> OTHER INFORMATION: (oligonucleotide primer)

<400> SEQUENCE: 6
cccggatccc gctgcttggc cttcttcac                                      29

<210> SEQ ID NO 7
<211> LENGTH: 15
<212> TYPE: PRT
<213> ORGANISM: Artificial
<220> FEATURE:
```

```
-continued

<223> OTHER INFORMATION: (partial sequence of SEQ ID NO.: 2)

<400> SEQUENCE: 7

Met Ala Gly Lys Lys Asn Val Leu Ser Ser Leu Ala Val Tyr Ala
1               5                   10                  15
```